(12) United States Patent
Crawford et al.

(10) Patent No.: US 11,338,088 B2
(45) Date of Patent: May 24, 2022

(54) VENTING SAFETY CLOSURE

(71) Applicant: Becton, Dickinson and Company, Franklin Lakes, NJ (US)

(72) Inventors: Jamieson W. Crawford, Hagersten (SE); Bradley M. Wilkinson, North Haledon, NJ (US); C. Mark Newby, Tuxedo, NY (US); Jitendra Ghanekar, Denville, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 405 days.

(21) Appl. No.: 16/111,786

(22) Filed: Aug. 24, 2018

(65) Prior Publication Data

US 2018/0361064 A1 Dec. 20, 2018

Related U.S. Application Data

(63) Continuation of application No. 13/491,988, filed on Jun. 8, 2012, now Pat. No. 10,086,140.

(60) Provisional application No. 61/495,573, filed on Jun. 10, 2011.

(51) Int. Cl.
*A61M 5/178* (2006.01)
*A61J 1/20* (2006.01)
*A61J 1/14* (2006.01)

(52) U.S. Cl.
CPC .......... *A61M 5/1782* (2013.01); *A61J 1/2096* (2013.01); *A61J 1/1425* (2015.05); *A61J 1/2075* (2015.05)

(58) Field of Classification Search
CPC ........................... A61M 5/1782; A61J 1/2096

USPC ........................................................ 600/576
See application file for complete search history.

(56) References Cited

U.S. PATENT DOCUMENTS

| 3,729,031 A | 4/1973 | Baldwin |
| 5,238,003 A * | 8/1993 | Baidwan ............ A61B 5/15003 600/578 |
| 5,429,256 A | 7/1995 | Kestenbaum |
| 5,573,525 A | 11/1996 | Watson et al. |
| 5,598,939 A | 2/1997 | Watson et al. |

(Continued)

FOREIGN PATENT DOCUMENTS

| FR | 2815328 A1 | 4/2002 |
| JP | 2004524914 A | 8/2004 |

(Continued)

*Primary Examiner* — Daniel L Cerioni
(74) *Attorney, Agent, or Firm* — The Webb Law Firm

(57) ABSTRACT

A closure for use with a specimen collection container is disclosed. The closure includes a base portion having a first end adapted for engagement with an open end of the specimen collection container, and a second end adapted for receiving a portion of a syringe assembly therein. The closure also includes a luer fitting connected to the base portion and having at least one channel for venting an interior of the specimen collection container to atmosphere during introduction of a fluid specimen from the syringe assembly into the specimen collection container. The closure further includes a shielding portion connected to the base portion and adapted to transition from an open position in which fluid communication is established between the first end and the second end through the luer fitting, to a closed position in which the luer fitting is fully shielded by the shielding portion.

19 Claims, 15 Drawing Sheets

(56) References Cited

U.S. PATENT DOCUMENTS

| | | | |
|---|---|---|---|
| 6,145,688 A | 11/2000 | Smith | |
| 6,491,667 B1 | 12/2002 | Keane et al. | |
| 6,832,994 B2 | 12/2004 | Niedospial, Jr. et al. | |
| 2002/0193777 A1 | 12/2002 | Aneas | |
| 2004/0199124 A1* | 10/2004 | Conte | A61M 5/3213 604/192 |
| 2004/0215106 A1 | 10/2004 | Sampson et al. | |
| 2007/0156112 A1* | 7/2007 | Walsh | A61J 1/2096 604/415 |
| 2008/0210890 A1* | 9/2008 | Fago | G21F 5/018 250/506.1 |
| 2008/0319345 A1 | 12/2008 | Swenson | |
| 2009/0216212 A1 | 8/2009 | Fangrow, Jr. | |
| 2009/0259145 A1* | 10/2009 | Bartfeld | A61B 10/0096 600/576 |
| 2010/0288694 A1* | 11/2010 | Crawford | B01D 17/0217 210/521 |
| 2011/0022023 A1 | 1/2011 | Weitzel et al. | |
| 2011/0139149 A1* | 6/2011 | Cacka | A61M 3/0262 128/200.14 |
| 2011/0168292 A1* | 7/2011 | Luzbetak | A61J 9/00 141/2 |

FOREIGN PATENT DOCUMENTS

| | | |
|---|---|---|
| WO | 9517874 A1 | 7/1995 |
| WO | 2009087572 A1 | 7/2009 |
| WO | 2009105489 A1 | 8/2009 |

\* cited by examiner

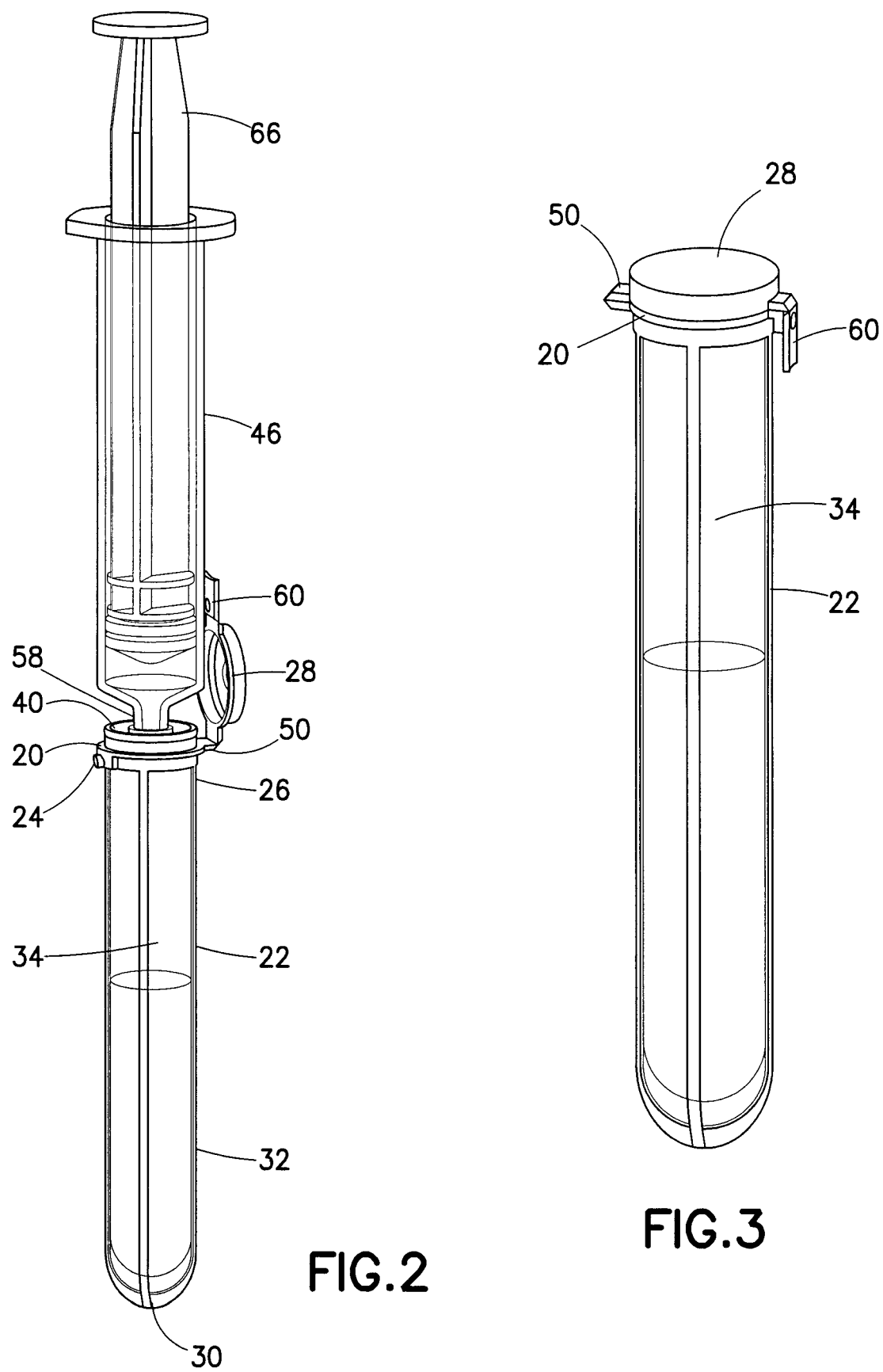

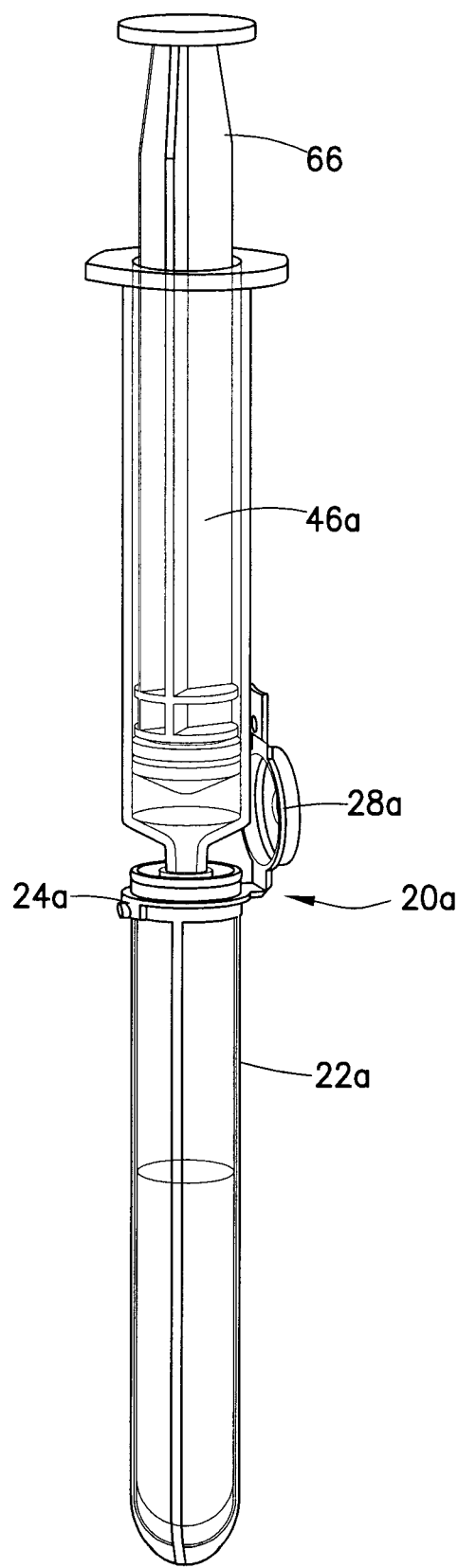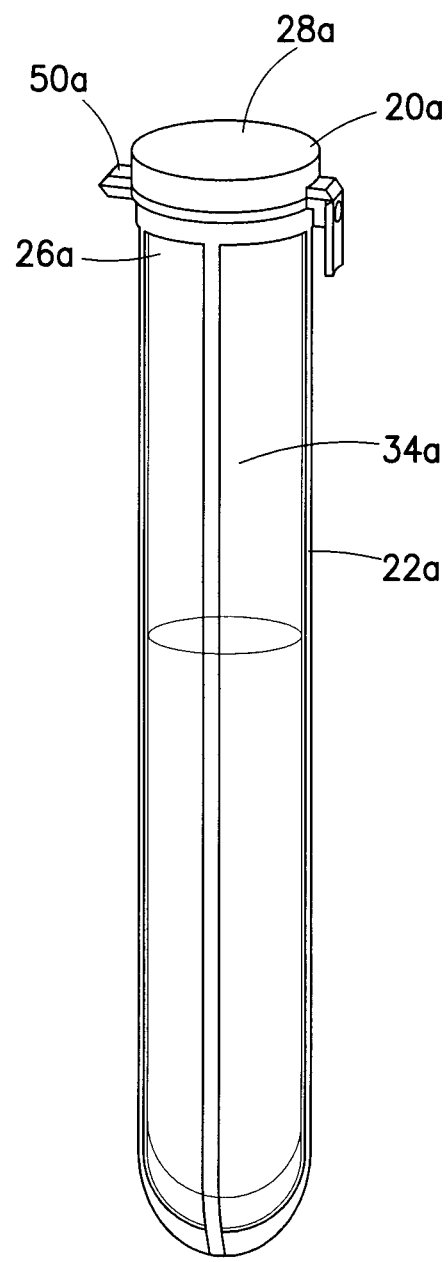
FIG.6
FIG.7

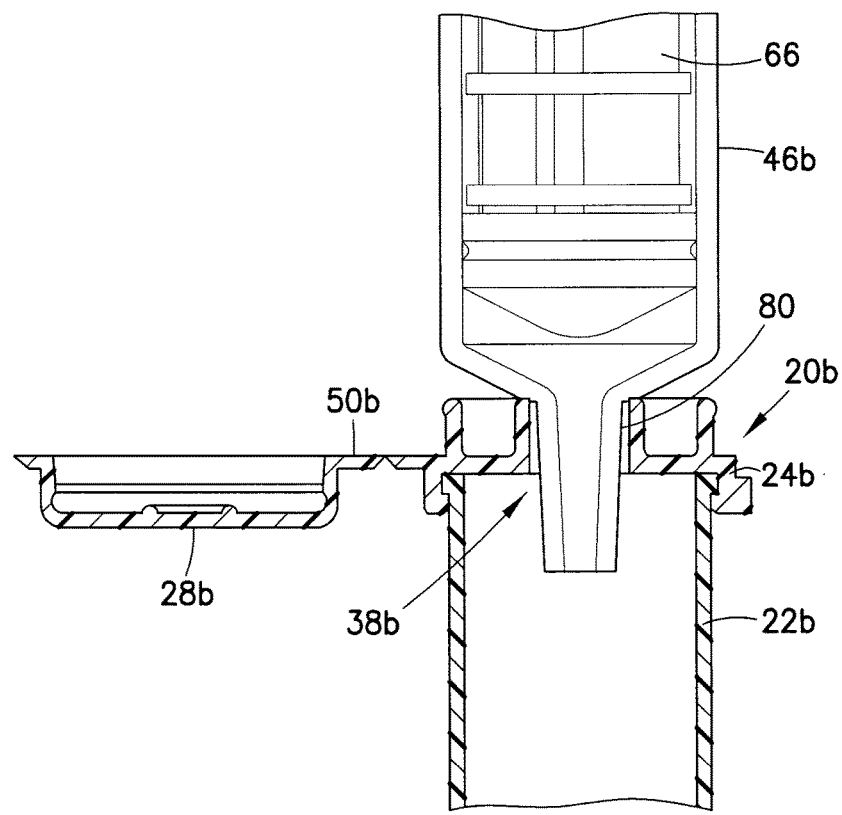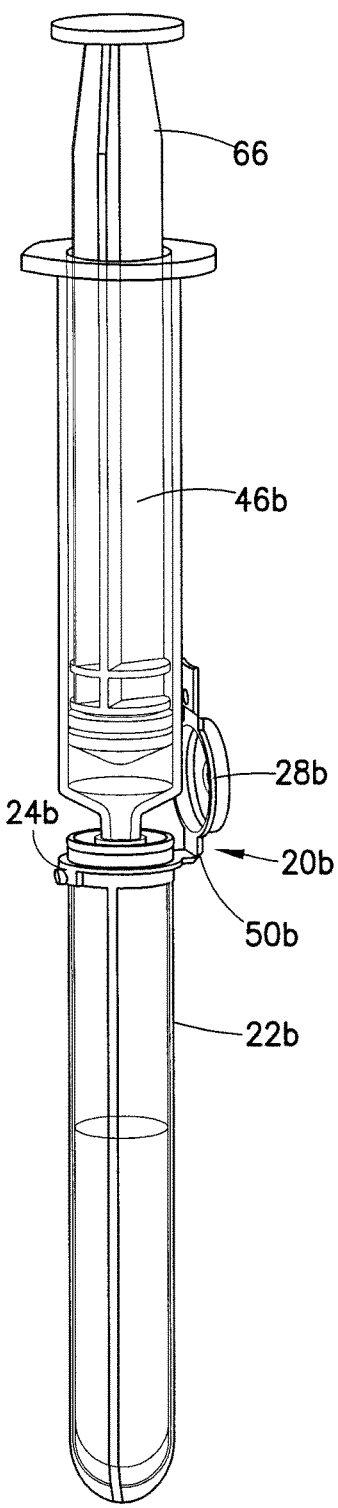
FIG.8
FIG.9

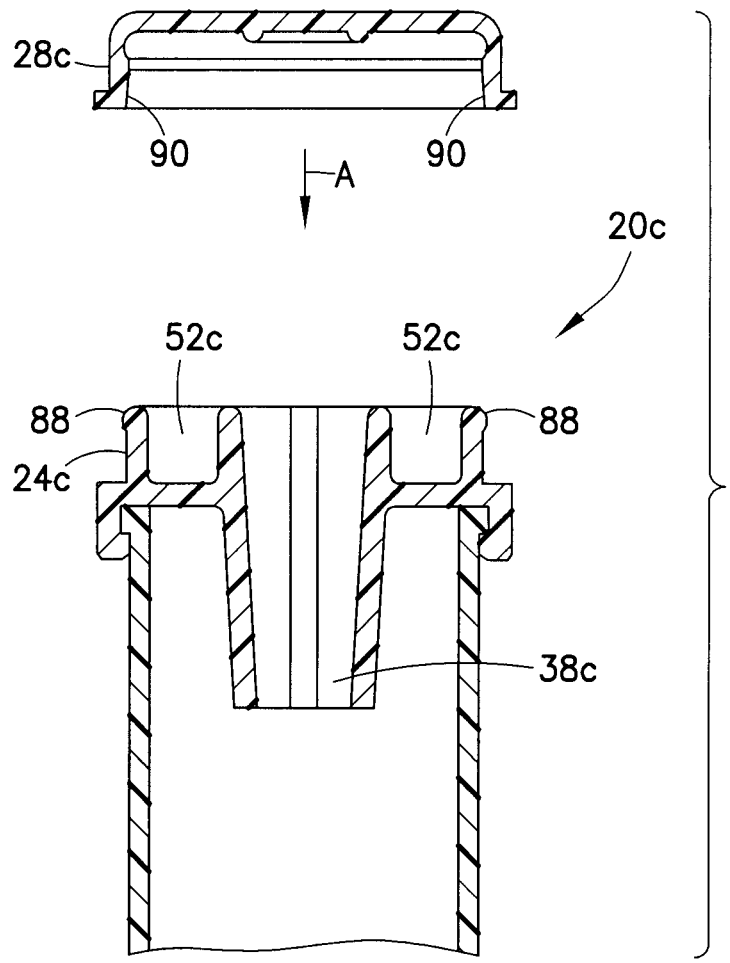
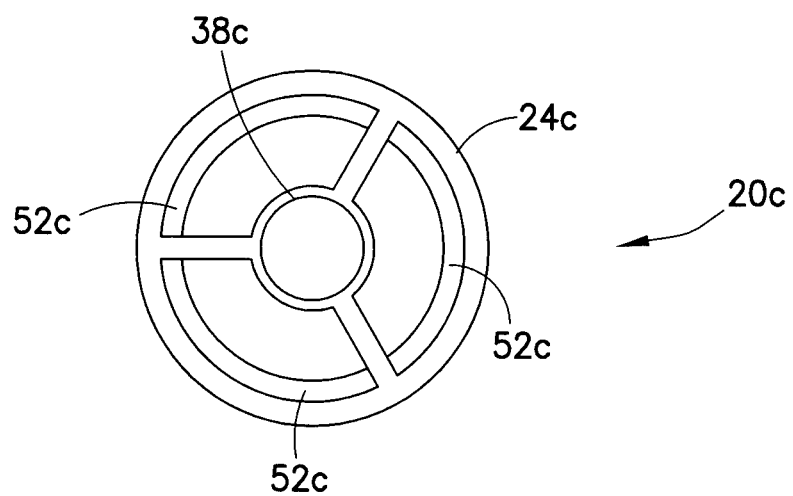
FIG. 10
FIG. 11

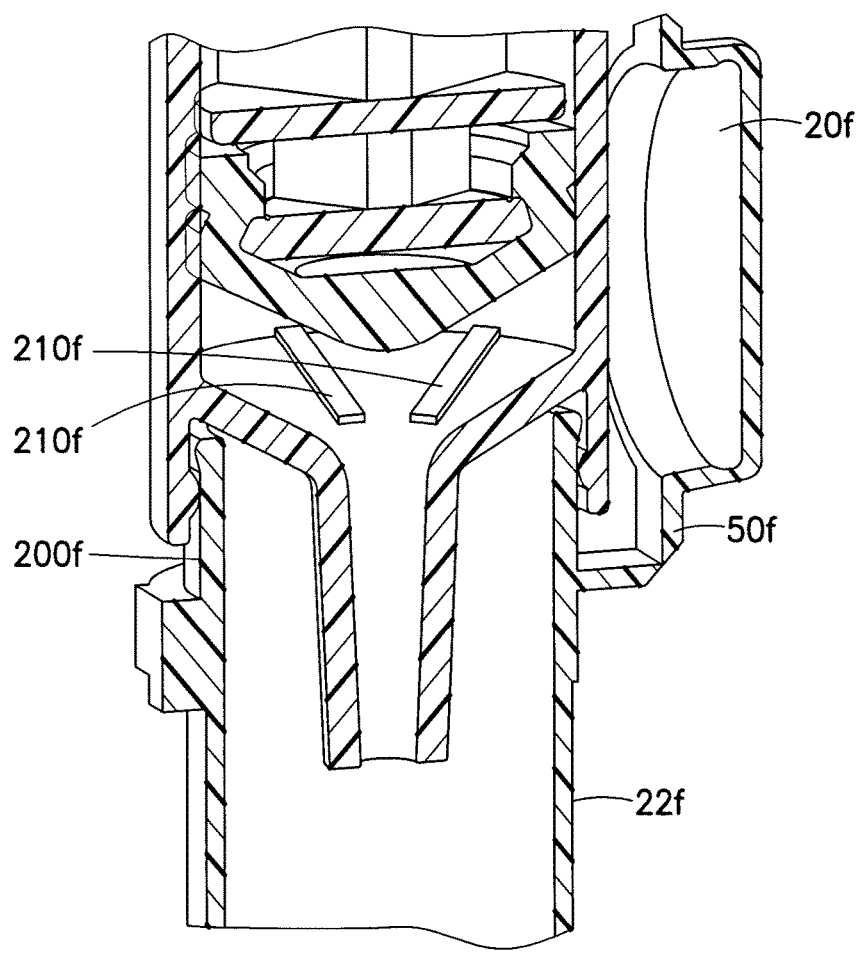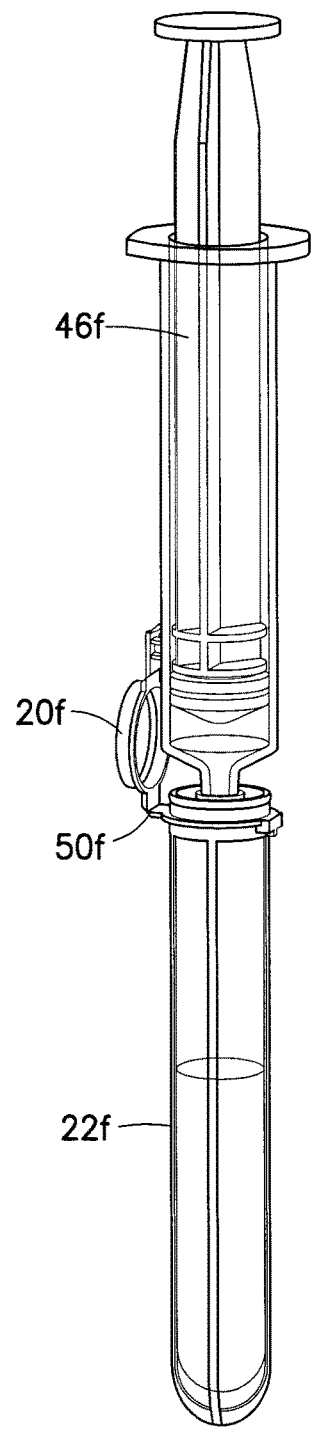
FIG.18
FIG.19

VENTING SAFETY CLOSURE

CROSS-REFERENCE TO RELATED APPLICATION

The present application is a continuation of U.S. patent application Ser. No. 13/491,988, entitled "Venting Safety Closure", filed Jun. 8, 2012, which claims the benefit of U.S. Provisional Application Ser. No. 61/495,573, entitled "Venting Safety Closure", filed Jun. 10, 2011, the entire disclosures of each of which are hereby incorporated by reference.

BACKGROUND OF THE INVENTION

Field of the Invention

The subject invention relates to a closure for a specimen collection container for receiving a fluid specimen therethrough from a syringe or other needle assembly. More particularly, this invention relates to a safety closure for a specimen collection container for limiting aerosolization of fluid and venting of air from within the specimen collection container during transfer of the fluid from the syringe into the specimen collection container.

Description of Related Art

Hypodermic syringes may be used in the medical arts for withdrawing fluid samples from a patient. Once a sample is collected within a syringe chamber, it may be desirable to transfer the collected sample into a specimen collection container for more stable handling or storage. With the recognition of fluid borne diseases that are transmitted by bodily fluids, and greater sensitivity of the need to protect healthcare workers from inadvertent contact with fluid samples and previously used needles (commonly referred to as "sharps"), a need has developed for specimen collection containers and closures having improved safety features. A specific need has developed for a closure suitable for use with a specimen collection container that minimizes exposure of healthcare practitioners to fluid samples and sharps during the transfer of a collected bodily fluid sample to a specimen collection container.

SUMMARY OF THE INVENTION

The present invention is directed to a closure for use with a specimen collection container having a base portion having a first end adapted for engagement with an open end of a specimen collection container, and a second end adapted for receiving a portion of a syringe assembly therein. The closure includes a luer fitting connected to the base portion and having at least one channel for venting an interior of the specimen collection container to atmosphere during introduction of a fluid specimen from the syringe assembly into the specimen collection container. The closure also includes a shielding portion connected to the base portion and adapted to transition from an open position in which fluid communication is established between the first end and the second end through the luer fitting, to a closed position in which the luer fitting is fully shielded by the shielding portion.

In certain configurations, the first end of the closure includes at least one deflectable rib for forming a substantially fluid-tight seal with a portion of the specimen collection container. The first end may also include an upper seal portion disposed to at least partially overlap an open end of the specimen collection container. The luer fitting may include a tapered surface for receiving a corresponding tapered surface of a syringe assembly therein. The luer fitting may also include a plurality of channels disposed thereabout to allow for venting an interior of the specimen collection container to atmosphere during introduction of a fluid specimen from the syringe assembly into the specimen collection container. Optionally, the channel may include a hydrophobic material therein. In certain configurations, the at least one channel is angled with respect to a surface of the first end.

In other configurations, the shielding portion is connected to the base portion by a spring element. The spring element may be a living hinge. The shielding portion may further include a lock tab and the base portion may further include a corresponding protrusion for engaging the lock tab in the closed position. In certain configurations, the at least one channel is an internal vent disposed within the luer fitting.

In accordance with another embodiment of the present invention, a closure for use with a specimen collection container includes a base portion having a first end adapted for engagement with an open end of a specimen collection container, and a second end adapted for receiving a portion of a syringe assembly therein. The closure also includes a luer fitting connected to the base portion and having at least one channel for venting an interior of the specimen collection container to atmosphere during introduction of a fluid specimen from the syringe assembly into the specimen collection container. Fluid communication is established between the first end and the second end through the luer fitting. The closure also includes a shielding portion connectable to the base portion to fully seal the luer fitting.

In certain configurations, the luer fitting includes a plurality of channels disposed thereabout to allow for venting an interior of the specimen collection container to atmosphere during introduction of a fluid specimen from the syringe assembly into the specimen collection container. Optionally, the channel includes a hydrophobic material therein. In other constructions, the at least one channel is angled with respect to a surface of the first end. The at least one channel may be an internal vent disposed within the luer fitting.

In accordance with another embodiment of the present invention, a specimen collection container includes a top end, a closed bottom end, and a sidewall extending therebetween defining an interior. The specimen collection container further includes a closure adapted to engage the top end, with the closure including a base portion having a first end adapted for engagement with the top end of the specimen collection container, and a second end adapted for receiving a portion of a syringe assembly therein. The closure also includes a luer fitting connected to the base portion and having at least one channel for venting an interior of the specimen collection container to atmosphere during introduction of a fluid specimen from the syringe assembly into the specimen collection container. The closure further includes a shielding portion connected to the base portion and adapted to transition from an open position in which fluid communication is established between the first end and the second end through the luer fitting, to a closed position in which the luer fitting is fully shielded by the shielding portion.

In certain configurations, the closure is permanently secured to the top end of the specimen collection container. Optionally, the luer fitting of the closure includes a plurality of channels disposed thereabout to allow for venting an interior of the specimen collection container to atmosphere during introduction of a fluid specimen from the syringe assembly into the specimen collection container. The at least one channel may be an internal vent disposed within the luer fitting.

In accordance with still a further embodiment of the present invention, a fluid transfer assembly includes a specimen collection container having a top end, a closed bottom end, and a sidewall extending therebetween defining an interior, and a closure adapted to engage the top end. The closure includes a base portion having a first end adapted for engagement with the top end of the specimen collection container, and a second end adapted for receiving a portion of a syringe assembly therein. The closure further includes a luer fitting connected to the base portion and having at least one channel for venting an interior of the specimen collection container to atmosphere during introduction of a fluid specimen from the syringe assembly into the specimen collection container. The closure also includes a shielding portion connected to the base portion and adapted to transition from an open position in which fluid communication is established between the first end and the second end through the luer fitting, to a closed position in which the luer fitting is fully shielded by the shielding portion. The second end of the closure includes a physical design feature. The fluid transfer assembly further includes a syringe assembly adapted for containing a fluid therein, wherein the syringe assembly includes a physical design feature for corresponding engagement with the physical design feature of the first end of the closure.

In certain configurations, the physical design feature of the second end of the closure includes one of a protrusion or recess and the physical design feature of the syringe assembly includes the other of the protrusion or recess, wherein the protrusion is adapted for receipt within the recess. In other configurations, the physical design feature of the second end of the closure comprises a saw-tooth pattern, and the physical design feature of the syringe assembly comprises a saw-tooth pattern for corresponding engagement with the saw-tooth pattern of the closure.

Further details and advantages of the invention will become clear from the following detailed description when read in conjunction with the accompanying drawings.

BRIEF DESCRIPTION OF THE DRAWINGS

FIG. 2 is a perspective front view of the closure, specimen collection container, and syringe assembly of FIG. 1 in accordance with an embodiment of the present invention.

FIG. 3 is a perspective front view of the closure and specimen collection container of FIG. 1 in the closed position in accordance with an embodiment of the present invention.

FIG. 6 is a perspective front view of the closure disposed within the specimen collection container of FIG. 4 engaged with a syringe assembly in accordance with an embodiment of the present invention.

FIG. 7 is a perspective front view of the closure disposed within the specimen collection container of FIG. 4 in the closed position in accordance with an embodiment of the present invention.

FIG. 8 is a partial cross-sectional perspective front view of a closure disposed within a specimen collection container and engaged with a syringe assembly in accordance with an embodiment of the present invention.

FIG. 9 is a perspective front view of the closure disposed within a specimen collection container and engaged with a syringe assembly of FIG. 8 in accordance with an embodiment of the present invention.

FIG. 10 is a partial cross-sectional front view of a closure disposed within a specimen collection container in accordance with an embodiment of the present invention.

FIG. 11 is a top view of the base portion of the closure of FIG. 10 in accordance with an embodiment of the present invention.

FIG. 18 is a partial cross-sectional front view of a closure disposed within a specimen collection container and engaged with a syringe assembly in accordance with an embodiment of the present invention.

FIG. 19 is a perspective view of the closure of FIG. 18 disposed within a specimen collection container and engaged with a syringe assembly in accordance with an embodiment of the present invention.

DETAILED DESCRIPTION OF THE INVENTION

Figure 1:
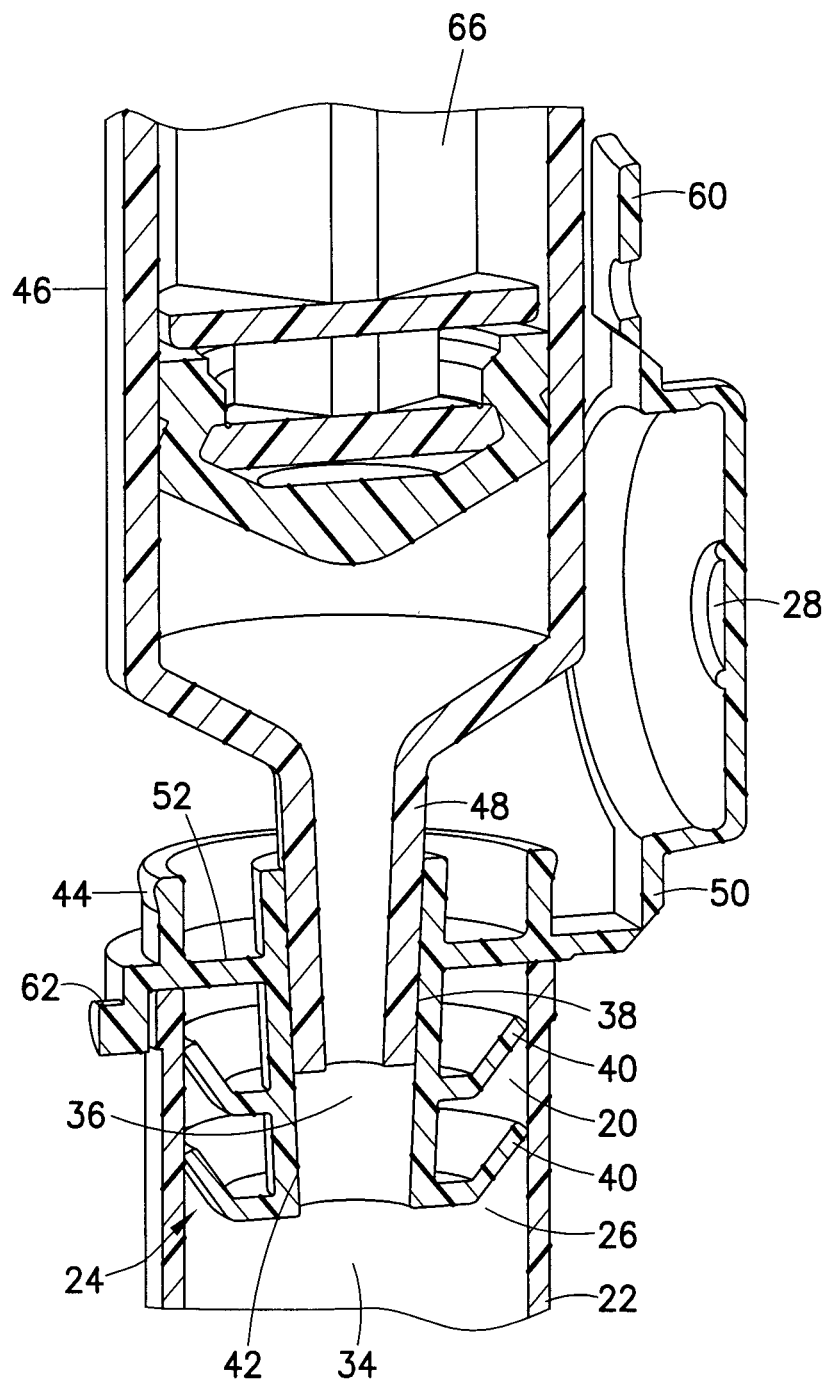
FIG. 1 is a partial cross-sectional front perspective view of a vented closure disposed within a specimen collection container and engaged with a syringe assembly in accordance with an embodiment of the present invention.

For purposes of the description hereinafter, the words "upper", "lower", "right", "left", "vertical", "horizontal", "top", "bottom", "lateral", "longitudinal", and like spatial terms, if used, shall relate to the described embodiments as oriented in the drawing figures. However, it is to be understood that many alternative variations and embodiments may be assumed except where expressly specified to the contrary. It is also to be understood that the specific devices and embodiments illustrated in the accompanying drawings and described herein are simply exemplary embodiments of the invention.

In accordance with an embodiment of the present invention, a closure 20 for a specimen collection container 22 is shown in FIGS. 1-3. The specimen collection container 22 may be any suitable collection container for receiving and storing a fluid sample, such as a bodily fluid, such as blood, therein. In one configuration, the specimen collection container 22 includes an open top end 26, a closed bottom end 30, and a sidewall 32 extending therebetween defining a container interior 34. The specimen collection container 22 may be made of any suitable materials, such as glass or polymeric materials, and may include one sidewall 32, or a plurality of sidewalls, such as a dual sidewall configuration.

The closure 20 includes a base portion 24 for insertion within the open top end 26 of the specimen collection container 22 and defines an opening 36 therethrough from an area outside the closure to the container interior 34. In one embodiment, the opening 36 includes a luer fitting 38 adapted to receive a corresponding portion of a syringe assembly therein. In another embodiment, the base portion 24 includes at least one deflectable rib 40 for forming a push-fit seal with a portion of the sidewall 32 of the specimen collection container 22. In a further embodiment, the deflectable rib 40 may form a substantially fluid tight seal with the sidewall 32 of the specimen collection container 22. In a further configuration, the base portion 24 of the closure 20 includes an upper seal portion 44 for overlapping the open top end 26 of the specimen collection container 22. In this configuration, the deflectable rib 40 of the base portion 24 may be disposed within the container interior 34 and the upper seal portion 44 contacts and extends at least partially over the open top end 26 of the specimen collection container 22. In a further embodiment, the base portion 24 of the closure 20 may include a deformable elastomeric component (not shown) to further assist in the sealing arrangement with the specimen collection container 22.

The opening 36 may extend through both the upper seal portion 44 and the base portion 24 to provide access through the closure 20 to the container interior 34. The luer fitting 38 of the closure 20 may include a v-shaped tapered surface 42 for receiving a corresponding tapered surface 48 of a syringe assembly 46 therein. The luer fitting 38 may be dimensioned to receive a portion of a housing 58 of the syringe assembly 46 therein, such as a distal portion of the syringe assembly 46 adjacent the opening.

The closure 20 may also include at least one channel 52 disposed about the luer fitting 38 to allow air to vent from within the container interior 34 when a fluid specimen is introduced into the container interior 34 through the opening 36 and/or luer fitting 38. In a further embodiment, a plurality of channels 52 may be disposed about the luer fitting 38 to maximize the venting of air. In still a further embodiment, the channels 52 may include a hydrophobic material to allow the passage of air therethrough and to restrain fluid from passing therethrough. In a further embodiment, the channels 52 may be physically dimensioned such that the surface tension of the fluid contained within the container interior 34 is sufficiently high to restrain fluid from passing through the channels 52. In a further configuration, a venting feature may be incorporated within the luer fitting 38, as will be discussed in detail herein.

As shown in FIGS. 1-3, the closure 20 may also include a top portion 28 connected to the base portion 24 through a spring element 50, such as a living hinge. Once transfer of a fluid sample from the syringe assembly 46 into the container interior 34 is complete, the syringe assembly 46 may be removed from the opening 36 and/or luer fitting 38 and the top portion 28 of the closure 20 may be engaged with the base portion 24, as shown in FIG. 3. The top portion 28 and the base portion 24 may be formed as a single piece closure 20. In a further configuration, the top portion 28 may have a lock tab 60 for engaging a corresponding protrusion 62 on the base portion 24 for forming a further seal for centrifugation and/or transport of the specimen collection container 22.

In certain configurations, the closure 20 of the present invention eliminates the need for a conventional shield to limit aerosolization during transfer of the fluid sample. The aerosolization of the fluid sample is limited because the closure 20 is flat with the open top end 26 of the specimen collection container 22 and as a result, no vacuum is generated within the specimen collection container 22 when the closure 20 is removed therefrom. This improvement contrasts with conventional closures which protrude a significant distance into the specimen collection container and result in the generation of a vacuum when the conventional closure is removed therefrom.

In a further configuration, the closure 20 may be dimensioned to have sufficient resistive force such that the closure 20 does not dislodge from the open top end 26 of the specimen collection container 22 when the syringe assembly 46 is removed from the closure 20.

In use, the closure 20 of the present invention is inserted into the open top end 26 of a specimen collection container 22 and a syringe assembly 46, having a fluid sample therein, is engaged within the opening 36 and/or luer fitting 38 of the closure 20. A user deploys a plunger 66 of the syringe assembly 46 to expel the contents of the syringe assembly 46 through the opening 36 and/or luer fitting 38 into the container interior 34. Simultaneously, air is vented from within the container interior 34 through the channels 52 to atmosphere. Once the fluid transfer is complete, the user removes the syringe assembly 46 from the closure 20 and flips the top portion 28 of the closure to engage the base portion 24 of the closure, and subsequently engages the lock tab 60 with the corresponding protrusion 62.

Figure 4:
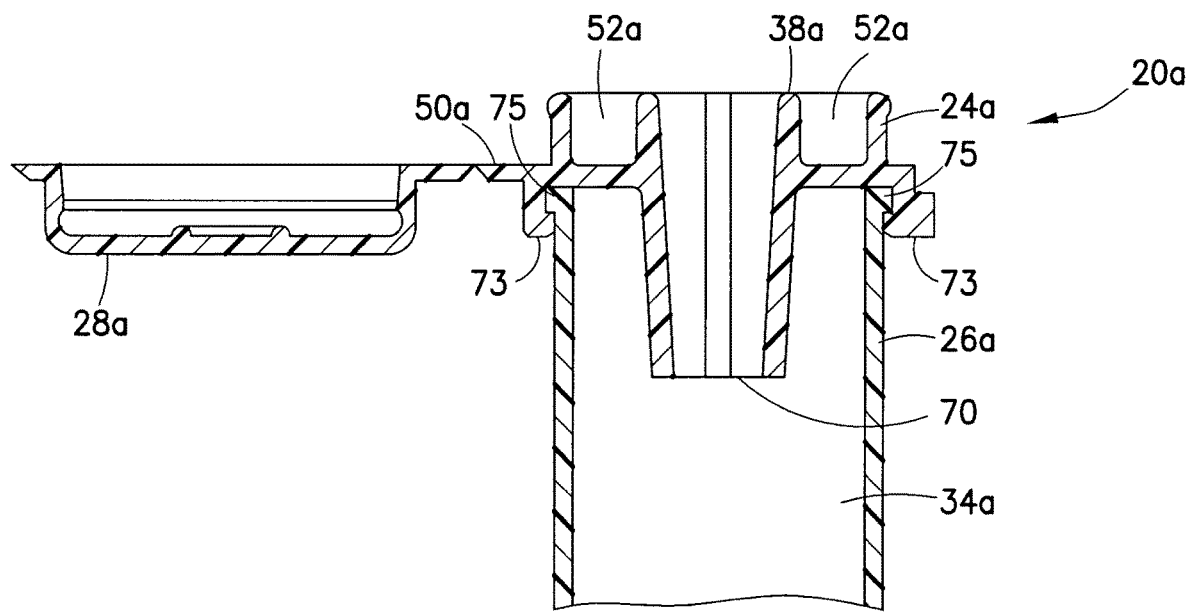
FIG. 4 is a partial cross-sectional front view of a closure disposed within a specimen collection container in accordance with an embodiment of the present invention.
Figure 5:
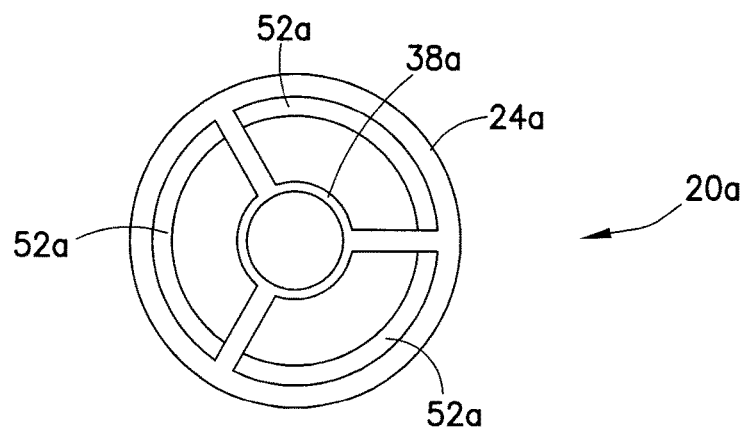
FIG. 5 is a top view of the base portion of the closure of FIG. 4 in accordance with an embodiment of the present invention.
Figure 12:
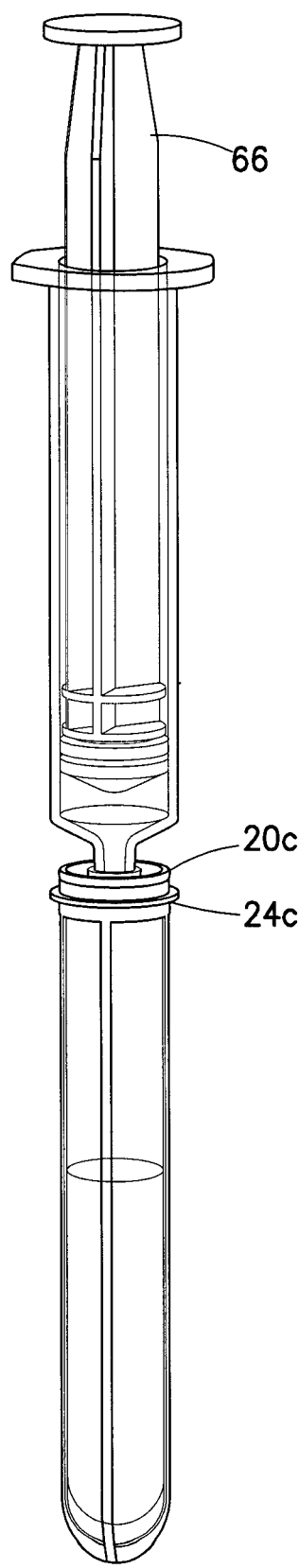
FIG. 12 is a perspective front view of the closure disposed within the specimen collection container of FIG. 10 engaged with a syringe assembly in accordance with an embodiment of the present invention.
Figure 13:
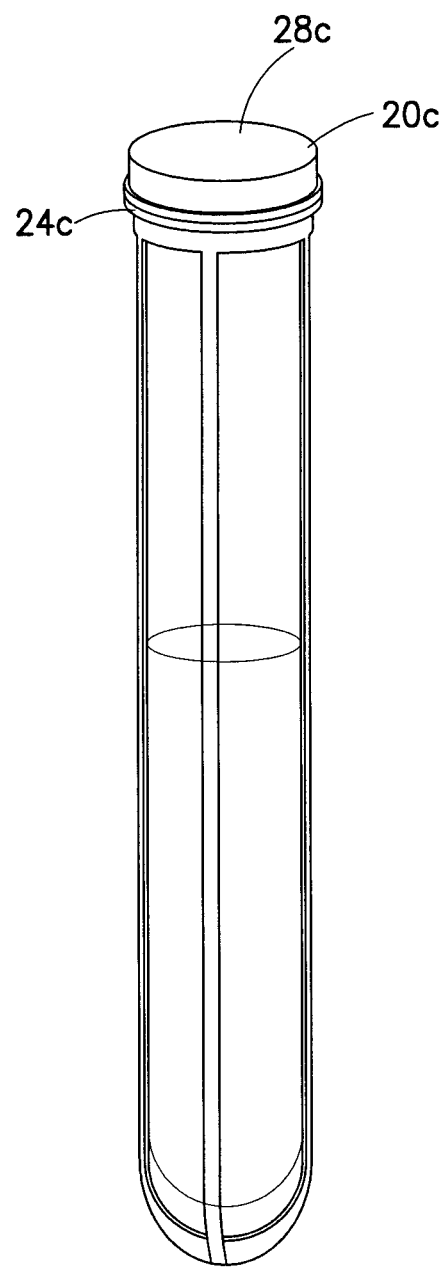
FIG. 13 is a perspective front view of the closure disposed within the specimen collection container of FIG. 10 in the closed position in accordance with an embodiment of the present invention.

In accordance with another embodiment of the present invention, as shown in FIGS. 4-7, a closure 20a includes a base portion 24a, a top portion 28a, and a spring element 50a, as discussed above. In this configuration, a luer fitting 38a may be surrounded by a plurality of channels 52a forming a star rib formation, as shown in FIG. 5. The star rib formation of channels may allow for the venting of air from within a container interior 34a of a container 22a, as discussed above, and for the optional pour-off of fluid sample. In a further configuration, the channels 52a may be angled to shed cells or other debris from the fluid sample.

Alternatively, as shown in FIGS. 4-7, the luer fitting 38a may be provided with an internal vent 70, as shown in FIG. 4, to allow the passage of air from within the container interior 34a at the same time that fluid sample is introduced through the luer fitting 38a from a syringe assembly 46a, as shown in FIG. 6. Optionally, as shown in FIG. 4, the base portion 24a of the closure 20a may include a snap ring 73 on the underside of the closure 20a for further securing the closure 20a to an upper rim 75 adjacent an open top end 26a of the specimen collection container 22a. In certain configurations, the closure 20a may be permanently attached to the specimen collection container 22a. This eliminates the problem of the closure 20a being inadvertently removed from the container 22a as the syringe assembly 46a is removed due to the high contact force between the luer fitting 38a of the closure 20a and the syringe assembly 46a.

In accordance with a further embodiment of the present invention, as shown in FIGS. 8-9, a closure 20b includes a base portion 24b, a top portion 28b, and a spring element 50b, as discussed above. In this configuration, a luer fitting 38b may be clearance fit with a syringe luer 80 of a syringe assembly 46b to reduce or greatly eliminate the pull back from the syringe assembly 46b upon removal of the syringe assembly 46b from the luer fitting 38b of the closure 20b, thereby reducing the instances of inadvertent removal of the closure 20b from a specimen collection container 22b. One benefit to this embodiment is that the luer fitting 38b is sufficiently large to allow a pipette or other instrument probe to be inserted therein for sample access.

In accordance with still a further embodiment of the present invention, as shown in FIGS. 10-13, a closure 20c includes a base portion 24c and a top portion 28c that is adapted for snap-fit engagement with the base portion 24c to cover channels 52c defined therein. In this configuration, the base portion 24c may include a protrusion 88 circumferentially disposed about a luer fitting 38c and extending radially outward therefrom. The top portion 28c may include a corresponding rim surface 90 for engaging the protrusion 88 of the base portion 24c when sufficient force is applied thereto in the direction of arrow A, as shown in FIG. 10. In this configuration, the engagement of the rim surface 90 and the protrusion 88 may be sufficient to withstand conventional centrifugation pressures.

Figure 14A:
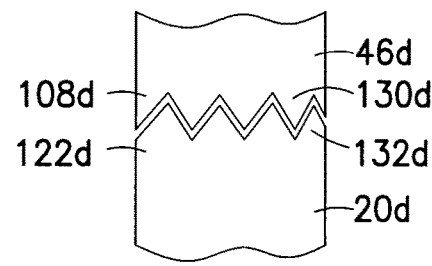
FIG. 14A is a partial representative front view of the design feature of a specimen collection container engaged with the design feature of a corresponding syringe assembly in accordance with an embodiment of the present invention.
Figure 14:
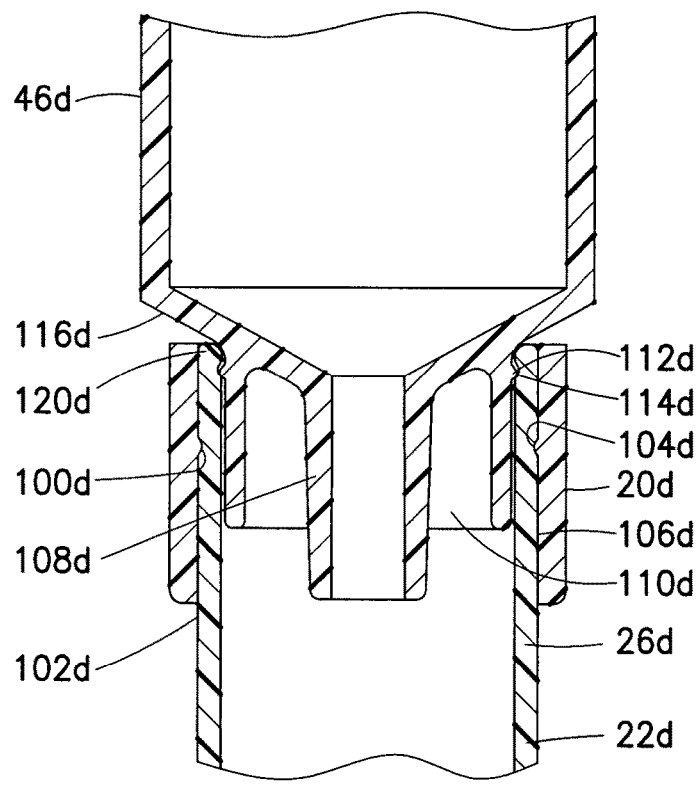
FIG. 14 is a partial cross-sectional front view of a closure disposed within a specimen collection container and engaged with a syringe assembly in accordance with an embodiment of the present invention.
Figure 15:
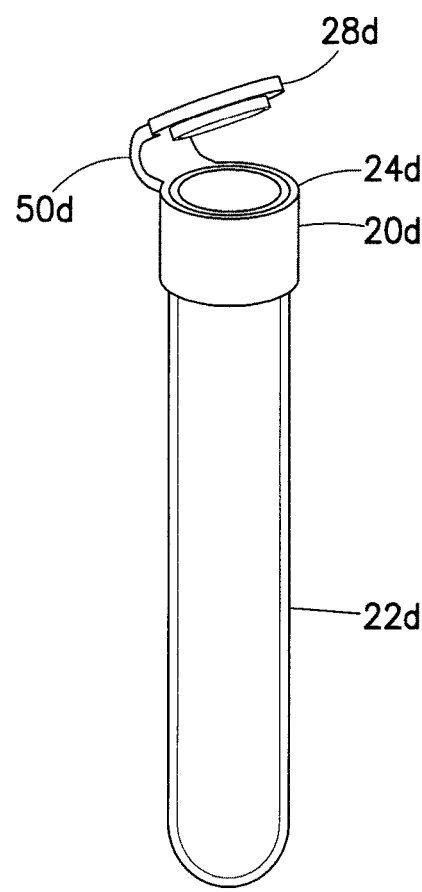
FIG. 15 is a perspective view of the closure of FIG. 14 engaged with a specimen collection container in accordance with an embodiment of the present invention.

In accordance with another embodiment of the present invention, as shown in FIGS. 14-15, a closure 20d may be permanently engaged over at least a portion of an open end 26d of a specimen collection container 22d. In this configuration, an annular protrusion 100d extends inwardly from an interior surface 102d of the closure 20d and a corresponding annular recess 104d may be formed on an outer surface 106d of the specimen collection container 22d adjacent the open end 26d. In one embodiment, the specimen collection container 22d may be formed of polypropylene and/or polyethylene and the recess 104d may be formed into the specimen collection container 22d during molding. In another configuration, the recess 104d may be formed within an interior surface if the specimen collection container 22d. Prior to receiving a specimen within the specimen collection container 22d, the closure 20d may be permanently engaged with the open end 26d of the specimen collection container 22d via a snap fit. It is noted herein, that in certain embodiments, the annular recess 104d and the annular protrusion 100d may be dimensioned to allow for the closure 20d to be removed from the specimen collection container 22d.

As shown in FIG. 14, during transfer of a specimen from a syringe assembly 46d into the specimen collection container 22d, a distal end 108d of the syringe assembly 46d may be received within an opening 110d of the closure 20d. In this configuration, the distal end 108d of the syringe assembly 46d may include an engagement protrusion 112d extending therearound for engagement with a corresponding engagement recess 114d defined within an interior portion of the specimen collection container 22d adjacent the open end 26d. In another configuration, the distal end 108d of the syringe assembly may include an engagement recess 114d and the interior portion of the specimen collection container 22d may include a corresponding engagement protrusion. Similarly, in another configuration, the engagement protrusion 112d of the syringe assembly 46d may be adapted for engagement with a portion of the interior of the closure 20d. In each of these configurations, a shoulder 116d of the syringe assembly 46d nests within a portion of the open end 26d of the specimen collection container 22d to minimize the collection of blood or other fluid specimen on a top rim 120d of the specimen collection container 22d.

In a further configuration, the snap engagement of the engagement protrusion 112d and the engagement recess 114d may be designed for a low release snap force, allowing easy insertion and removal of the distal end 108d of the syringe assembly 46d with the closure 20d. In still a further configuration, the snap engagement of the engagement protrusion 112d and the engagement recess 114d may incorporate a venting feature adapted to allow egress of air from within the interior of the specimen collection container 22d to vent therethrough during the introduction of fluid sample into the interior of the specimen collection container 22d through the closure 20d. The dimensioning of the opening 110d of the closure 20d allows for full access of instrument probes and pipettes, and allows the user to pour off specimen sample, if desired.

In accordance with a further embodiment, as shown in FIG. 14A, a design feature 130d may be applied/incorporated within the syringe assembly 46d adjacent the distal end 108d for corresponding mating or contact with a design feature 132d applied to/incorporated within the closure 20d, adjacent a top portion 122d. The design features 130d, 132d may have any correspondingly forming attribute, such as a saw-tooth or other pattern, intended to suggest to the user of the closure 20*d* that a needle cannula, if present, should be removed from the syringe assembly 46*d* prior to the engagement of the syringe assembly 46*d* with the closure 20*d*. In this configuration, the design feature 130*d* of the body of the syringe assembly 46*d* may be duplicated in the design feature 132*d* of the closure, indicating to the user to remove the needle cannula so as to mate the corresponding design features 130*d*, 132*d*. In a further configuration, the design features 130*d*, 132*d* may include a physical modification to the distal end 108*d* of the syringe assembly 46*d* and the top portion 122*d* of the closure 20*d* for physical contact or engagement therewith absent a needle cannula. In another configuration, the design features 130*d*, 132*d* may include visual features for providing proper engagement or contact between the closure 20*d* and the syringe assembly 46*d* absent a needle cannula.

In still a further configuration, the design feature 130*d* applied to the syringe assembly 46*d* may be applied to the shoulder 116*d* and include a feature that would indicate to the user that the engagement between the syringe assembly 46*d* and the closure 20*d* is not a luer lock. Example design features 130*d* suitable for evidencing a non-luer lock engagement include a cut out disposed within the shoulder 116*d* to provide a non-continuous cylinder. In still a further embodiment, the opening 110*d* or luer feature within the closure 20*d* may be offset from center so as to evidence to a user that the engagement between the closure 20*d* and the syringe assembly 46*d* is not a luer lock. In addition, the offset luer feature helps to transfer the sample in such a manner that, as the sample exits the luer of the syringe, it is guided to travel down the inside wall of the specimen collection container 22*d*, which acts to reduce the frothing of the sample and in turn acts to reduce hemolysis of the sample.

In each of these embodiments, the design features 130*d*, 132*d* are intended to prompt the user to remove a needle cannula from the syringe assembly 46*d* prior to transferring a specimen into the specimen collection container 22*d* through the closure 20*d* in order to reduce hemolysis and improve user safety. A further benefit of the design features 130*d*, 132*d* is to make the closure/specimen collection container system more intuitive and easy to use. Specifically, the goal is to encourage the user to mate the luer or distal end 108*d* of the syringe assembly 46*d* with the luer or opening 110*d* of the closure 20*d*. As discussed in detail above, the closure 20*d*, as shown in FIG. 15, may include a base portion 24*d* and a top portion 28*d* connected by a spring element 50*d* to form a flip-cap. The design feature 132*d* may be incorporated within one or both of the base portion 24*d* and the top portion 28*d*. The flip cap feature of the closure 20*d* can seal with the specimen collection container 22*d* by sharing the same undercut snap feature of the opening 110*d* of the specimen collection container 22*d* during closure as the syringe assembly 46*d* during transfer.

Figure 16:
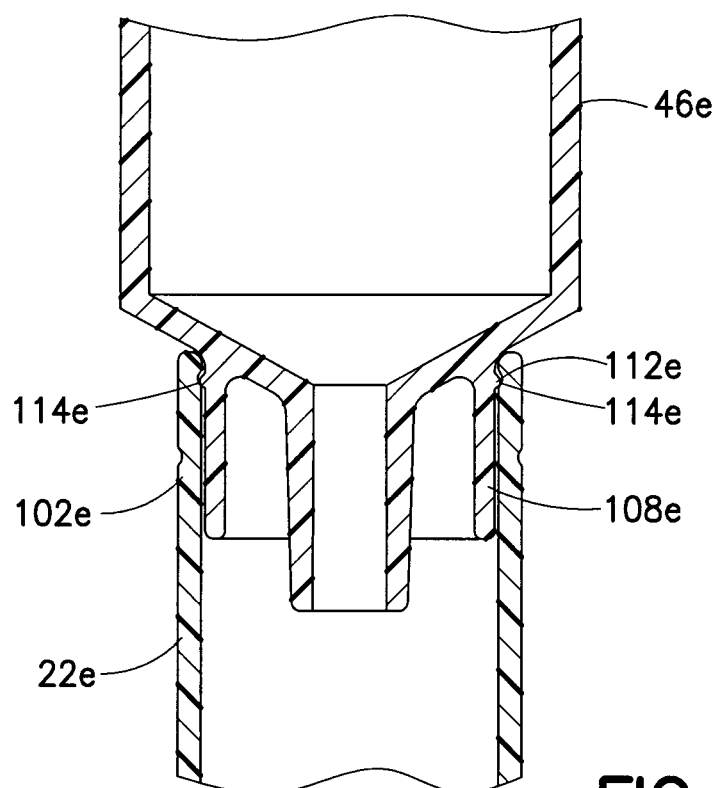
FIG. 16 is a partial cross-sectional front view of a closure disposed within a specimen collection container and engaged with a syringe assembly in accordance with an embodiment of the present invention.
Figure 17:
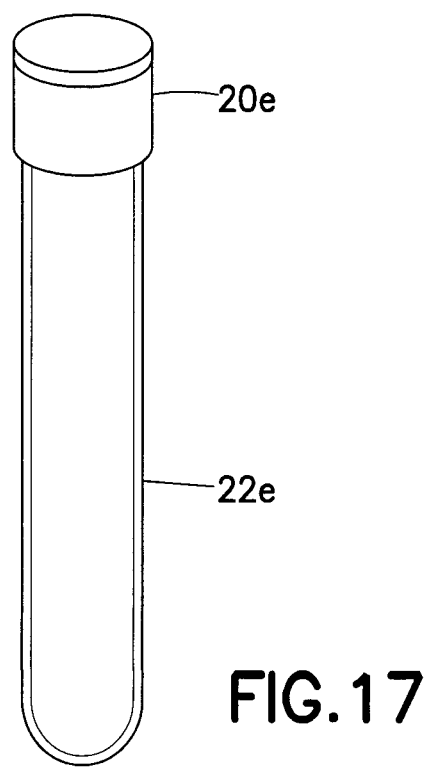
FIG. 17 is a perspective view of the closure of FIG. 16 engaged with a specimen collection container in accordance with an embodiment of the present invention.

In still a further configuration, as shown in FIGS. 16-17, it is possible to insert a distal end 108*e* of a syringe assembly 46*e* directly within an open top end 102*e* of a specimen collection container 22*e*. In this configuration, an engagement protrusion 112*e* of the syringe assembly 46*e* directly engages an engagement recess 114*e* molded within the interior of the specimen collection container 22*e* adjacent the open top end 102*e*. Once a sample is introduced into the specimen collection container 22*e*, and the syringe assembly 46*e* is removed therefrom, a separate snap cap closure 20*e* may be disposed over the open top end 102*e* of the specimen collection container 22*e* to seal the contents therein, as shown in FIG. 17.

In yet another configuration, as shown in FIGS. 18-19, a specimen collection container 22*f* and a closure 20*f* may be formed as a single unit with a spring element 50*f* disposed therebetween. In this configuration, the closure 20*f* is permanently affixed to the specimen collection container 22*f* to reduce instances in which the closure 20*f* is inadvertently removed from the specimen collection container upon removal of a syringe assembly 46*f* therefrom after introduction of a sample therein.

An advantage of the flip-cap feature of the closure 20*f* is that it simplifies the sample transfer process. With a non flip-cap closure, the user is required to remove the closure, place the closure separate from the tube during transfer, pick up the closure after transfer, and then re-apply the closure. With the flip-cap closure 20*f*, the user can, with one hand, hold the specimen collection container and flip the closure open and with the other hand, hold the syringe assembly and transfer the sample, and then flip the cap closed again with the first hand. Several work process steps are eliminated, which allows for a faster process of sample transfer. In addition, the flip-cap closure 20*f* greatly reduces the possibility of cross contamination that occurs with a non flip-cap closure in the situation when a user inadvertently replaces a different patient's cap on the tube. This cross contamination issue is one source of sample analysis error.

In the configuration shown in FIGS. 18-19, the syringe assembly 46*f* may be provided to engage a portion of the closure 20*f* and/or specimen collection container 22*f* on an exterior surface 200*f* through a plurality of corresponding ribs 210*f*. In a further embodiment, the ribs 210*f* may include a venting aspect to allow air to vent from within the interior of the specimen collection container 22*f* therethrough during introduction of a specimen from the syringe assembly 46*f*. Nesting the syringe assembly 46*d*, 46*f* within either the inside of the specimen collection container 22*d*, as shown in FIGS. 14-15, or the outside of the specimen collection container 22*f*, as shown in FIGS. 18-19, allows for the "closed" transfer of the sample from the syringe assembly 46*d*, 46*f* to the specimen collection container 22*d*, 22*f*, which acts to minimize exposure of the healthcare worker to the sample.

In a further embodiment, the specimen collection container 22*f* and the closure 20*f* may be formed as a single unit with an integral tether disposed therebetween. The tether may be integral with the closure and may be formed of a thin flexible connector. In one configuration, the tether may have a rectangular cross section with a thickness of about 0.02-0.2" and a width of about 0.095". The tether configuration is applicable as an alternate embodiment to all flip-cap versions described.

Figure 20:
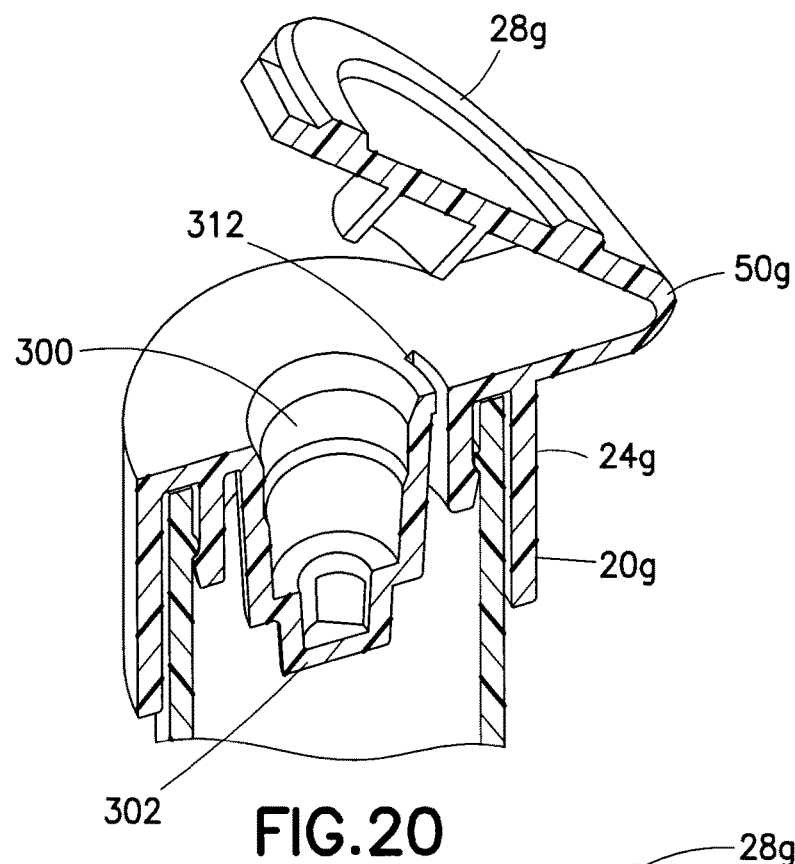
FIG. 20 is a partial cross-sectional perspective view of a closure disposed within a specimen collection container in accordance with an embodiment of the present invention.
Figure 21:
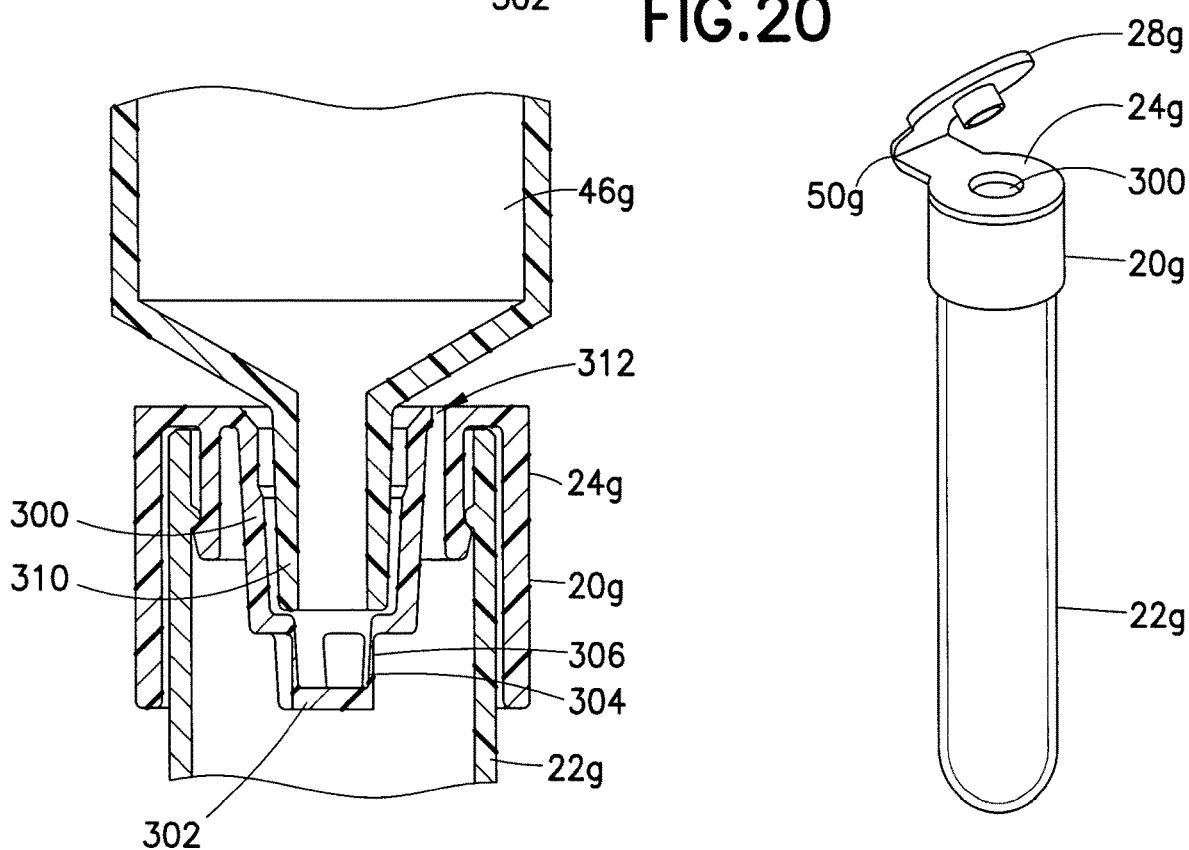
FIG. 21 is a partial cross-sectional front view of the closure of FIG. 20 disposed within a specimen collection container and engaged with a syringe assembly in accordance with an embodiment of the present invention.
Figure 22:
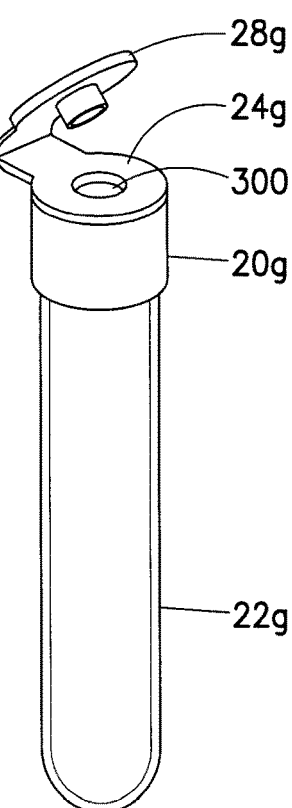
FIG. 22 is a perspective view of the closure of FIG. 20 engaged with a specimen collection container in accordance with an embodiment of the present invention.

Referring now to FIGS. 20-22, a closure 20*g* in accordance with another embodiment of the present invention includes features as previously described and includes an opening 300 dimensioned to allow a clearance fit with a pipette tip. In this configuration, a shelf 302 is provided at a bottom end 304 of the opening 300 to prevent a needle cannula (not shown) or other sharp from passing beyond the bottom end 304 of the opening 300 of the closure 20*g*. This configuration prevents a user from transferring a fluid sample from a syringe assembly 46*g* into a specimen collection container 22*g* while a needle cannula is attached thereto. At least one access opening 306 is provided adjacent the shelf 302 to allow passage of fluid sample into the interior of the specimen collection container 22*g* through the opening 300 while a needle cannula or other sharp is restrained from entering the specimen collection container 22*g*. In certain configurations, the dimensioning of the shelf 302 may also prevent taper lock between a portion of the opening 300 of the closure 20g and a corresponding taper of a distal end 310 of the syringe assembly 46g during specimen transfer. A vent 312 may also be integrated into the inside of the luer fitting and/or opening 300 of the closure 20g. Alternatively, as indicated in FIG. 21, the vent 312 may be located adjacent the luer fitting.

In one configuration, the closure 20g may be snap fit with a portion of the specimen collection container 22g, as discussed above. Alternatively, the snap feature may be disposed on the outside wall of the specimen collection container 22g and the corresponding surface of the closure 20g. In another configuration, both the closure 20g and a portion of the outer surface of the specimen collection container may include corresponding threads for enabling rotational engagement and disengagement of the closure 20g and specimen collection container 22g. In either embodiment, the closure 20g may include a base portion 24g and a top portion 28g connected by a spring element 50g. When the top portion 28g of the closure 20g is secured with the base portion 24g, both the opening 300 and the vent 312 are effectively sealed from atmosphere. The closure 20g may also be designed to eliminate negative space within the underside of the closure 20g so as to facilitate the shedding of cells and other material. This may be accomplished in part by providing an elastomeric feature within any in-molded cavities within the underside of the closure 20g, or by introducing rib geometry that eliminates the internal spaces.

In accordance with a further embodiment, the luer feature within the closure is off center and access opening 306 is configured such that a blood sample is guided to travel down the inside surface of the tube wall. This acts to reduce frothing of the sample and minimize hemolysis. In an alternate embodiment, shelf 302 is removed, allowing an instrument probe/pipette to be inserted beyond the closure for sample access.

Figure 23:
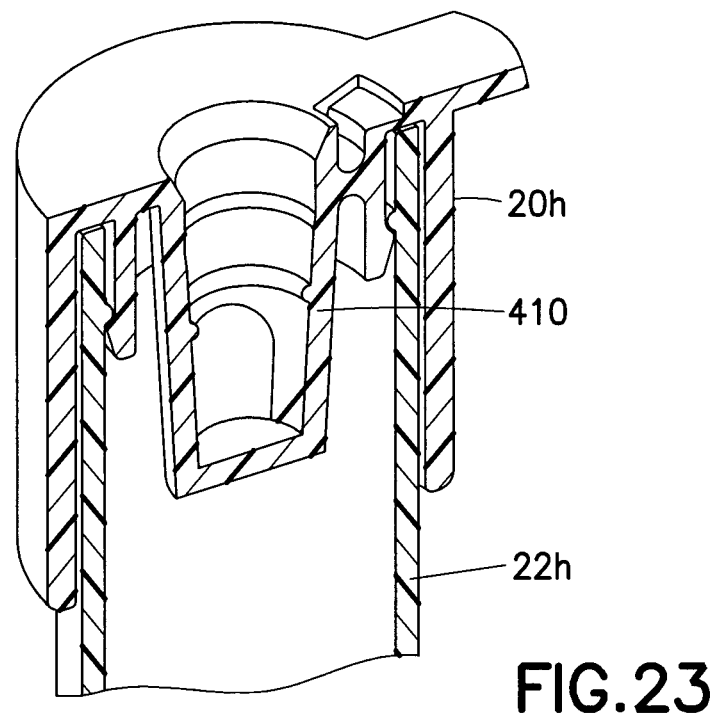
FIG. 23 is a partial cross-sectional perspective view of a closure disposed within a specimen collection container in accordance with an embodiment of the present invention.
Figure 24:
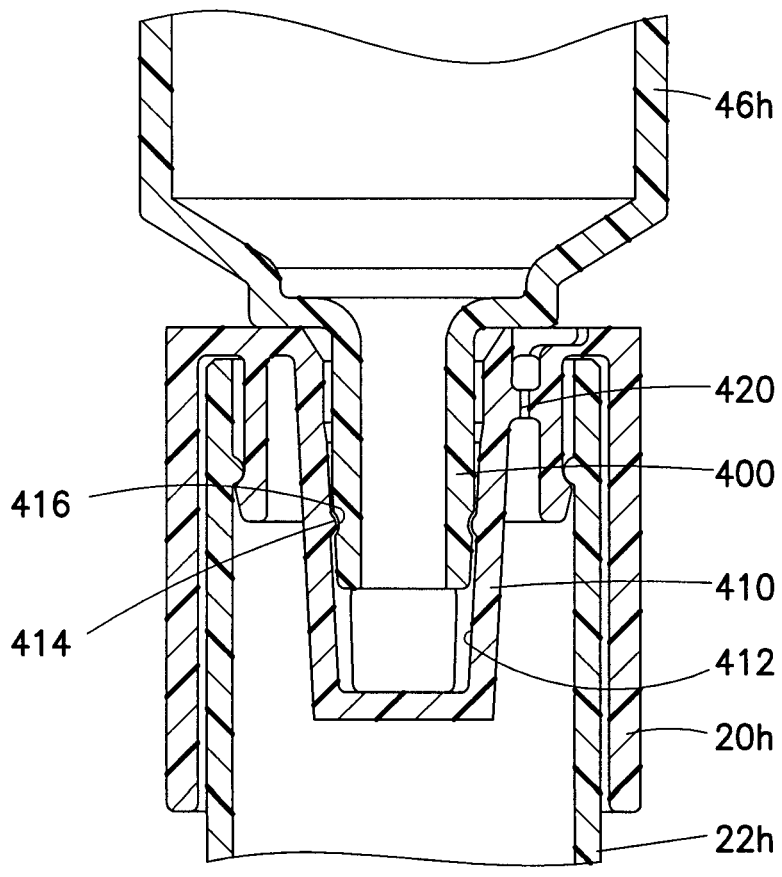
FIG. 24 is a partial cross-sectional front view of the closure of FIG. 23 disposed within a specimen collection container and engaged with a syringe assembly in accordance with an embodiment of the present invention.
Figure 25:
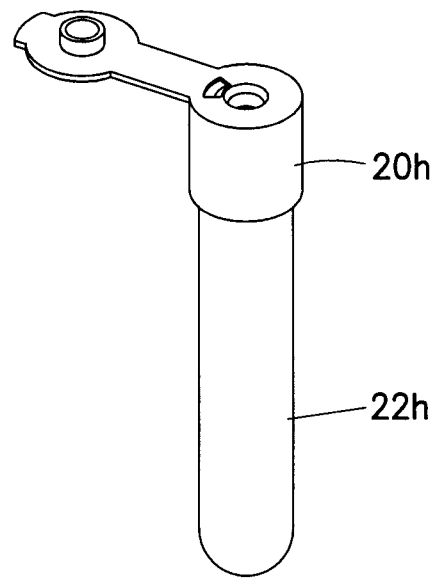
FIG. 25 is a perspective view of the closure of FIG. 23 engaged with a specimen collection container in accordance with an embodiment of the present invention.

In accordance with still a further embodiment of the present invention, as shown in FIGS. 23-25, a luer 400 of a syringe assembly 46h may be nested inside a luer 410 of a closure 20h in a snap-fit engagement. In this configuration, an interior surface 412 of the luer 410 of the closure 20h may include a luer protrusion 414 for engaging a corresponding luer recess 416 disposed within the luer 400 of the syringe assembly 46h. In this configuration, the engagement between the luer 400 of the syringe assembly 46h and the luer 410 of the closure 20h may have a low snap force such that removal of the syringe assembly 46h from the closure 20h does not result in the inadvertent removal of the closure 20h from a specimen collection container 22h. Alternatively, the closure 20h and the specimen collection container 22h may be provided with correspondingly engaging threads for threaded engagement to reduce instances of inadvertent removal of the closure 20h from the specimen collection container 22h during removal of the syringe assembly 46h from the closure 20h. With specific reference to FIG. 24, a vent feature 420 may be incorporated within closure 20h adjacent the luer 410 to provide for the venting of air from within the specimen collection container 22h, as discussed above.

Figure 25A:
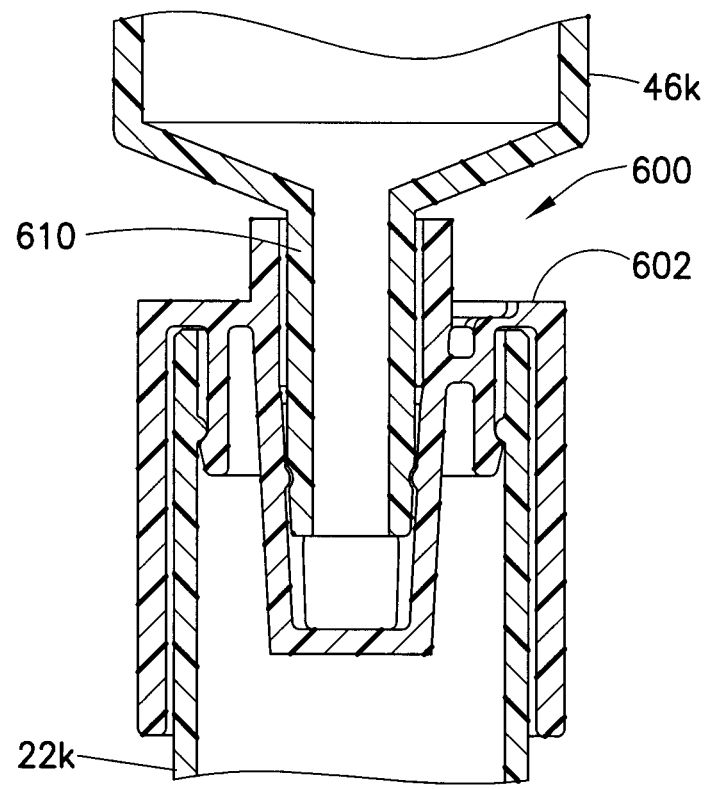
FIG. 25A is a partial cross-sectional front view of a closure disposed within a specimen collection container engaged with a syringe assembly in accordance with an embodiment of the present invention.

In accordance with another embodiment, as shown in FIG. 25A, a portion of a luer 600 of a specimen collection container 22k is raised above a top surface 602 of the specimen collection container 22k to provide a visual cue to the user to insert a luer 610 of a syringe assembly 46k into the closure.

Figures 26, 27:
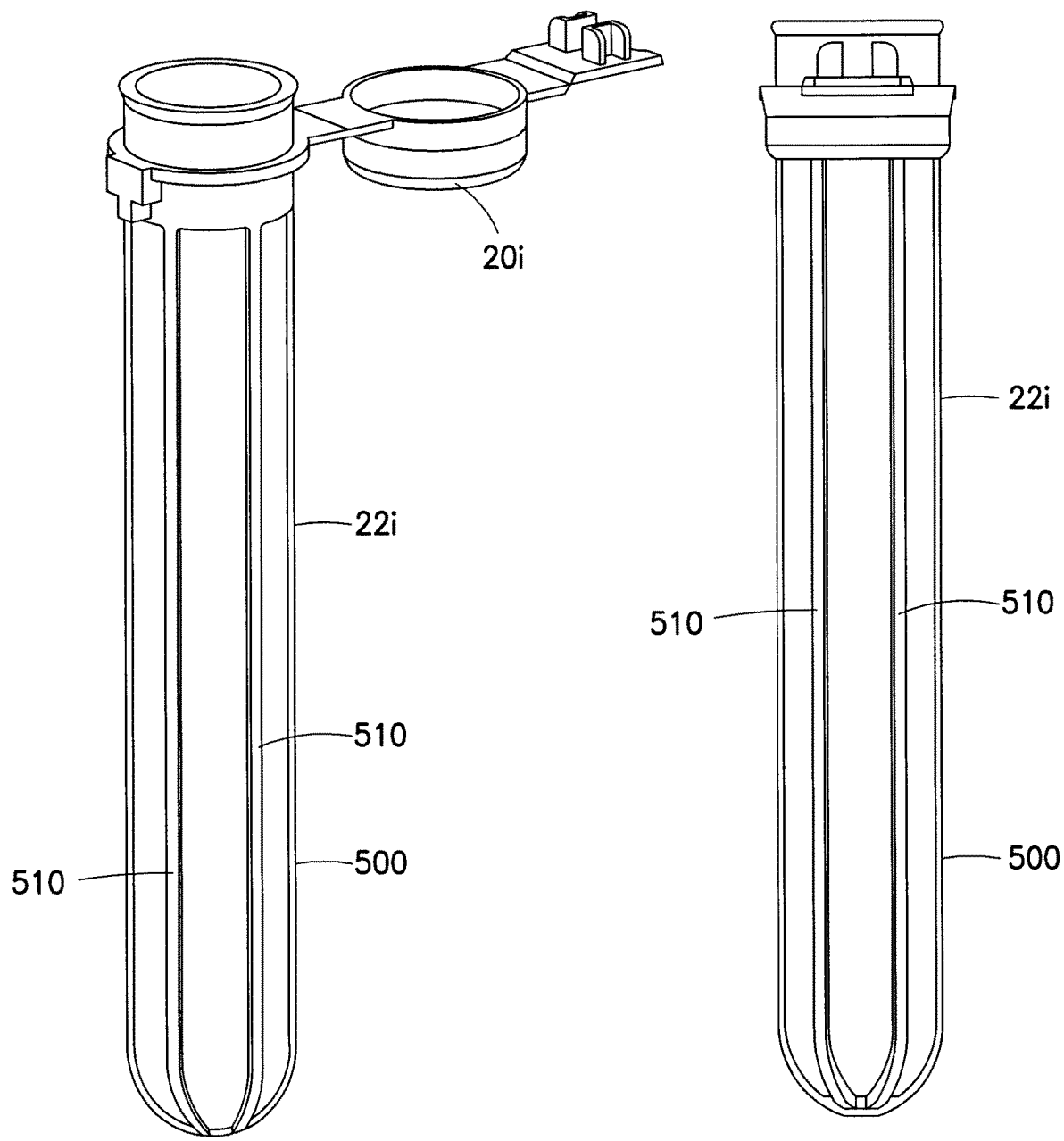
FIG. 26 is a perspective view of a closure engaged with a specimen collection container in accordance with the present invention.
FIG. 27 is a front view of the closure disposed within the specimen collection container of FIG. 26 in accordance with an embodiment of the present invention.
Figure 28:
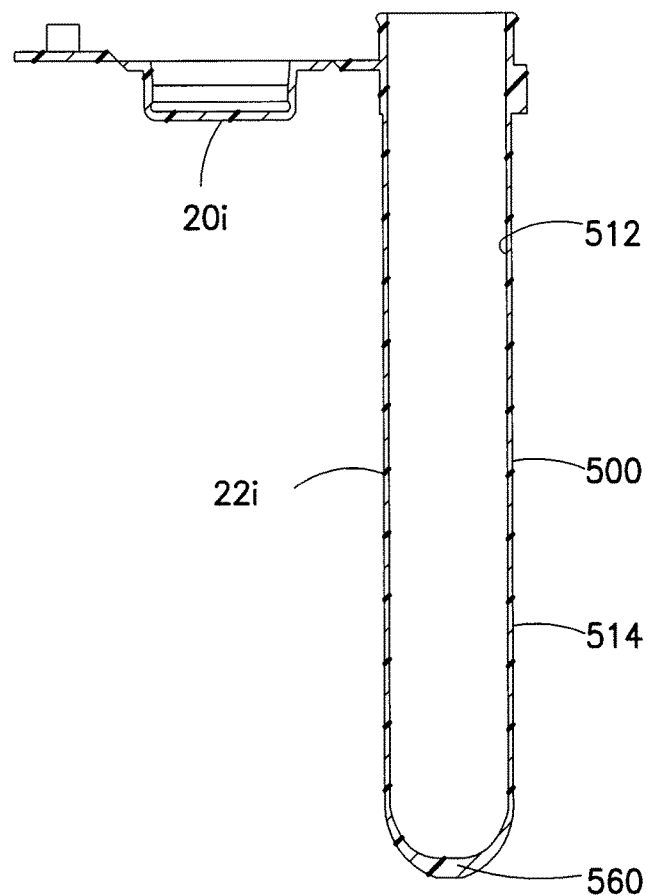
FIG. 28 is a cross-sectional side view of the closure disposed within the specimen collection container of FIG. 26 taken along line x-x of FIG. 27 in accordance with an embodiment of the present invention.
Figure 29:
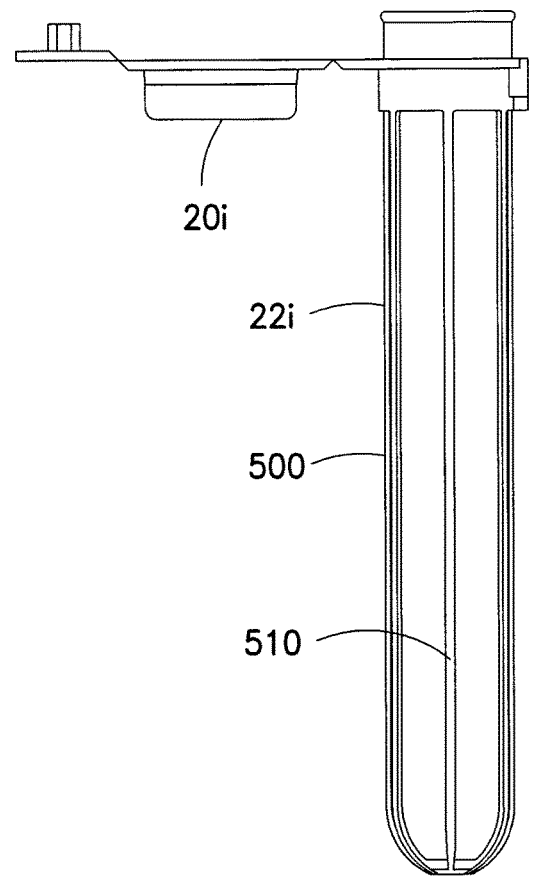
FIG. 29 is a side view of the closure disposed within the specimen collection container of FIG. 26 in accordance with an embodiment of the present invention.
Figure 30:
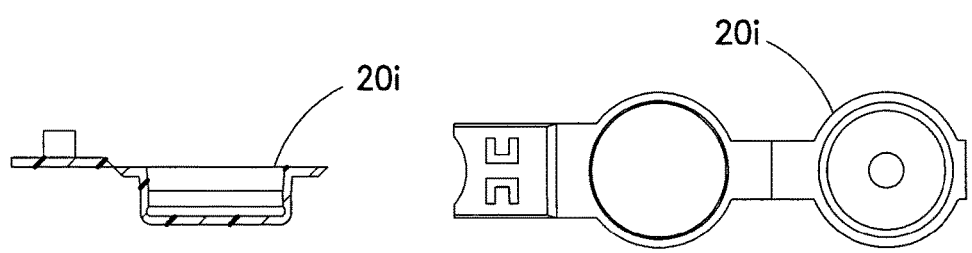
FIG. 30 is a side view of the closure of FIG. 26 in accordance with an embodiment of the present invention.
Figure 31:
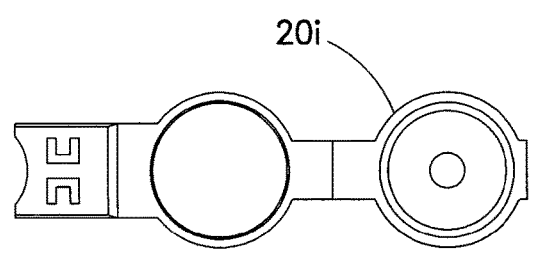
FIG. 31 is a top view of the closure of FIG. 26 in accordance with an embodiment of the present invention.

It is noted herein that the closures described herein may be suitable for a number of different specimen collection containers, including non-evacuated specimen collection containers. Accordingly, the closures described herein do not need to support a vacuum within the specimen collection container that is required to be maintained over the shelf-life of the specimen collection container. In addition, the specimen collection containers suitable for use with the closures described herein do not need to support the internal pressures associated with the maintenance of an internal vacuum. Accordingly, in one embodiment of the present invention, as shown in FIGS. 26-31, a novel specimen collection container 22i and an associated closure 20i may include material saving features for reducing the overall cost required during manufacture. As shown in FIGS. 26-27 and 29, a sidewall 500 of the specimen collection container 22i may be formed of a thin wall of material, such as in the range of 0.010" to 0.025" material thickness, and is supported by a plurality of strengthening ribs 510. The strengthening ribs 510 may be provided at appropriate intervals about the circumference of the sidewall 500 to provide sufficient rigidity to the specimen collection container 22i to allow a specimen to be received and stored therein, while minimizing the amount of material required for manufacture. The specimen collection container 22i may also include a base portion 560, as shown in FIG. 28, having a thicker wall section to provide resistance in the event the specimen collection container 22i is dropped on the floor.

In one embodiment, as shown in FIG. 28, the strengthening ribs 510 may be provided on an interior surface 512 of the sidewall 500 to allow for a smooth exterior surface 514 of the sidewall, such as for the application of a label (not shown) thereon. In another configuration, the strengthening ribs 510 may be provided on exterior surface 514 of the sidewall to allow for the shedding of cells and other material along the interior surface 512 of the sidewall 500. The thin walled specimen collection container 22i may be used with any of the closures 20, as discussed herein.

It is also noted herein that the closures described herein may be color coded to signify the type of specimen collection container functionality, such as, for example, chemistry tubes, as is standard existing practice. It is also noted herein that the closures described herein may be suitable for use with a wide variety of syringe assemblies, including syringe assemblies having a retractable needle in which the needle cannula is retracted into the housing of the syringe after use. A kit of parts including a syringe assembly, such as a retractable needle syringe, and a specimen collection container having a closure as described herein associated therewith may be provided together.

While the present invention is described with reference to several distinct embodiments of a venting safety closure and method of use, those skilled in the art may make modifications and alterations without departing from the scope and spirit. Accordingly, the above detailed description is intended to be illustrative rather than restrictive.

What is claimed is:

1. A specimen collection container, comprising:
   a top end, a closed bottom end, and a sidewall extending therebetween defining an interior; and
   a closure adapted to engage the top end, the closure comprising:
   a base portion comprising a first end adapted for engagement with the top end of the specimen collection container, and a second end adapted for receiving a portion of a syringe assembly therein, the first end comprising (1) at least one deflectable rib inseparable from the closure forming a push-fit and fluid-tight seal with an inner surface of the sidewall through direct contact of the at least one deflectable rib with the inner surface of the sidewall wherein contact of the deflectable rib with the inner surface of the sidewall pivots the tip of the deflectable rib radially inward and upward toward the top end of the specimen collection container when the first end is inserted within the top end, and (2) an upper seal portion that contacts and extends at least partially over the top end;

a luer fitting connected to the base portion and comprising at least one channel for venting the interior of the specimen collection container to atmosphere during introduction of a fluid specimen from the syringe assembly into the specimen collection container; and a shielding portion connected to the base portion and adapted to transition from an open position in which fluid communication is established between the first end and the second end through the luer fitting, to a closed position in which the luer fitting is fully shielded by the shielding portion.

2. The specimen collection container of claim 1, wherein the closure is secured to the top end of the specimen collection container by a snap fit.

3. The specimen collection container of claim 1, wherein the luer fitting comprises a plurality of channels disposed thereabout to allow for venting the interior of the specimen collection container to atmosphere during introduction of the fluid specimen from the syringe assembly into the specimen collection container.

4. The specimen collection container of claim 1, wherein the at least one channel is an internal vent disposed within the luer fitting.

5. The specimen collection container of claim 1, wherein the luer fitting comprises a tapered surface for receiving a corresponding tapered surface of the syringe assembly therein.

6. The specimen collection container of claim 3, wherein each of the plurality of channels provides a separate vent from the other channels directly connecting the interior of the container to atmosphere.

7. The specimen collection container of claim 1, wherein the at least one channel includes a hydrophobic material.

8. The specimen collection container of claim 1, wherein the at least one channel is angled with respect to a surface of the first end.

9. The specimen collection container of claim 1, wherein the shielding portion is connected to the base portion by a spring element.

10. The specimen collection container of claim 9, wherein the spring element is a living hinge.

11. The specimen collection container of claim 1, wherein the shielding portion further comprises a lock tab and the base portion further comprises a corresponding protrusion for engaging the lock tab in the closed position.

12. The specimen collection container of claim 1, wherein the at least one channel is an external vent disposed entirely outside the outer circumference of the luer fitting to allow for venting the interior of the specimen collection container to atmosphere during introduction of the fluid specimen from the syringe assembly into the specimen collection container.

13. A fluid transfer assembly, comprising:
a specimen collection container comprising a top end, a closed bottom end, and a sidewall extending therebetween defining an interior; and
a closure adapted to engage the top end, the closure comprising:
a base portion comprising a first end adapted for engagement with the top end of the specimen collection container, and a second end adapted for receiving a portion of a syringe assembly therein, the first end comprising (1) at least one deflectable rib inseparable from the closure forming a push-fit and fluid-tight seal with an inner surface of the sidewall through direct contact of the at least one deflectable rib with the inner surface of the sidewall wherein contact of the deflectable rib with the inner surface of the sidewall pivots the tip of the deflectable rib radially inward and upward toward the top end of the specimen collection container when the first end is inserted within the top end, and (2) an upper seal portion that contacts and extends at least partially over the top end;
a luer fitting connected to the base portion and comprising at least one channel for venting the interior of the specimen collection container to atmosphere during introduction of a fluid specimen from the syringe assembly into the specimen collection container; and
a shielding portion connected to the base portion and adapted to transition from an open position in which fluid communication is established between the first end and the second end through the luer fitting, to a closed position in which the luer fitting is fully shielded by the shielding portion,
wherein the second end of the closure includes a first physical design feature, and
wherein the syringe assembly includes a second physical design feature for corresponding engagement with the physical design feature of the second end of the closure.

14. The fluid transfer assembly of claim 13, wherein the first physical design feature of the second end of the closure includes one of a protrusion or recess and the second physical design feature of the syringe assembly includes the other of the protrusion or recess, wherein the protrusion is adapted for receipt within the recess.

15. The fluid transfer assembly of claim 13, wherein the first physical design feature of the second end of the closure comprises a saw-tooth pattern, and the second physical design feature of the syringe assembly comprises a saw-tooth pattern for corresponding engagement with the saw-tooth pattern of the second end of the closure.

16. The fluid transfer assembly of claim 13, wherein the luer fitting comprises a tapered surface for receiving a corresponding tapered surface of the syringe assembly therein.

17. The fluid transfer assembly of claim 13, wherein the at least one channel is a plurality of channels, and wherein each of the plurality of channels provides a separate vent from the other channels directly connecting the interior of the container to atmosphere.

18. The fluid transfer assembly of claim 13, wherein the at least one channel includes a hydrophobic material.

19. The fluid transfer assembly of claim 13, wherein the at least one channel is angled with respect to a surface of the first end.

* * * * *